July 9, 1957 W. KORDES Plant Pat. 1,618
ROSE PLANT
Filed Nov. 14, 1956
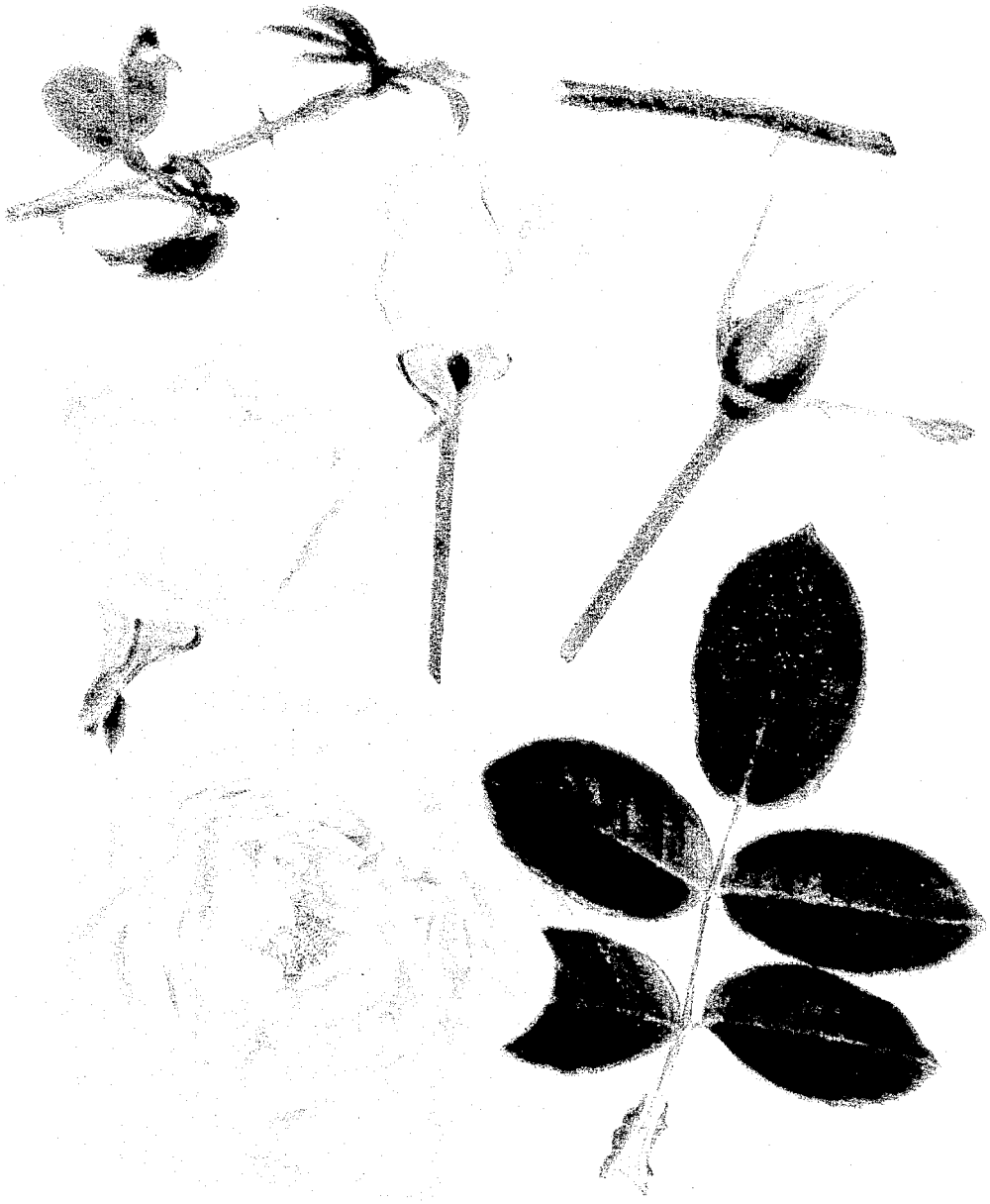
Inventor.
Wilhelm Kordes
By: Robb & Robb
Attorneys.

United States Patent Office

Plant Pat. 1,618
Patented July 9, 1957

1,618

ROSE PLANT

Wilhelm Kordes, near Elmshorn in Holstein, Sparrieshoop, Germany, assignor to Jackson & Perkins Company, Newark, N. Y., a corporation of New York Application November 14, 1956, Serial No. 622,231

1 Claim. (Cl. 47—61)

The present invention relates to a new and distinct variety of rose plant of the hybrid tea class, which was originated by me by crossing the variety "R. M. S. Queen Mary" (Plant Patent No. 249) with the variety "Viktoria Adelheid" (unpatented).

The primary objective of this cross was to produce a new rose variety embodying the form and attractiveness of the parent "R. M. S. Queen Mary," combined with the characteristics of a better and improved plant and foliage.

This objective was fully achieved, as evidenced by the fact that the new variety is characterized by the excellence of the plant; leathery, glossly foliage; very large, well-formed buds and flowers; attractive two-toned bud color corresponding to Pale Orange Yellow, with the upper half of the petals lightly overcast with Thulite Pink; the distinctive color of the flowers which is Deep Rose Pink, lightly overcast with Spinel Pink on the inside of the flower petals and Cream color on the reverse of the flower petals, with the outer edge of the petals lightly overcast with Cameo Pink; and the distinctive Thulite Pink general color tonality of the flowers at the end of the third day, which is characteristic of the parent variety "Viktoria Adelheid."

Considered together, the foregoing characteristics and distinctions definitely differentiate my new variety from its parents, as well as from all other varieties of its class of which I am aware, and represent a unique combination in a hybrid tea rose.

Asexual reproduction of the new variety by budding, as performed at Newark, New York, U. S. A., and also at Pleasanton, California, U. S. A., shows that the foregoing characteristics and distinctions come true to form and are established and transmitted through succeeding propagations.

The accompanying drawing shows typical specimens of the vegetative growth and flowers of my new variety in different states of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"R. M. S. Queen Mary."
*Pollen parent.*—"Viktoria Adelheid."
Classification:
*Botanic.*—Hybrid tea.
*Commercial.*—Hybrid tea.

*Flower*

(Observations made from specimens grown outdoors at Newark, New York, U. S. A., in the early morning of the latter part of July.)
Blooming habit: Recurrent; continuous.
Bud:
*Size.*—Large.
*Form.*—Ovoid; is not affected by wet or hot weather.

*Color.*—When sepals first divide—Rose Doree, Plate 1. When petals begin to unfurl—Geranium Pink, Plate 1. When half-blown: inside of petals—Spinel Pink, Plate 26, lightly overcast with Deep Rose Pink, Plate 12; reverse of petals—Pale Orange Yellow, Plate 3, with upper half of petal lightly overcast with Thulite Pink, Plate 26.
*Sepals.*—Slightly branched; curl back when petals begin to unfurl. Color: inside—Light Fluorite Green, Plate 32; outside—Biscay Green, Plate 17.
*Calyx.*—Color—Chromium Green, Plate 32. Shape—apple. Size—broad. Aspect—smooth. Odor when rubbed—none.
*Peduncle.* — Length — medium. Aspect — rough. Strength—erect; heavy. Color—Light Elm Green, Plate 17.
*Opening.*—Opens up well; is not affected by adverse weather conditions.
Bloom:
*Size.*—Very large. Average size when fully expanded—from 5 to 5½ inches.
*Borne.*—Both singly and several together.
*Stems.*—Long; strong.
*Form (when first open).*—High center. Permanence—retains its form to the end, but outer petals curl back.
*Petalage.*—Very double (many petals and stamens hidden). Number of petals under normal conditions—from 50 to 55.
*Color.*—Center of flower—Spinel Pink, Plate 26, lightly overcast with Deep Rose Pink, Plate 12. Outer petals—Thulite Pink, Plate 26, lightly overcast with Spinel Pink, Plate 26, on the outer edge of the petal. Base of petals (aiglet)—Picric Yellow, Plate 4. Inside of petals—Deep Rose Pink, Plate 12, lightly overcast with Spinel Pink, Plate 26. Reverse of petals—Cream color, Plate 16, with outer edge of petal lightly overcast with Cameo Pink, Plate 26. General tonality from a distance—Spinel Pink, Plate 26, lightly overcast with Thulite Pink, Plate 26.
*Discoloration.*—General tonality at end of first day—Deep Rose Pink, Plate 12. Second day—Thulite Pink, Plate 26, lightly overcast with Deep Rose Pink, Plate 12. Third day—Thulite Pink, Plate 26.
Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.* — Moderate. Nature — tea (average hybrid tea scent).
*Lasting quality.*—On the plant—long. As cut flower—long.

*Genital organs*

Stamens, Anthers: Large; many; regularly arranged around styles. Color—Light Cadmium Yellow, Plate 4.
Stamens, filaments (threads): Long. Color—Flame Scarlet, Plate 2.
Pollen: Color—Maize Yellow, Plate 4.
Styles: Loosely separated; medium length; thin.
Stigmas: Color—Picric Yellow, Plate 4.
Ovaries: All enclosed in calyx.
Hips: None.
Seeds: None.

*Plant*

Form: Bush.
Growth: Vigorous; upright; compact.
Foliage: Compound of 5 to 7 leaflets.
*Size.*—Large.
*Quantity.*—Normal.
*Color.*—New foliage: upper side—Oil Green, Plate 5, lightly overcast with Oxblood Red, Plate 1; under side—Yellowish Oil Green, Plate 5, lightly overcast with Oxblood Red, Plate 1. Old foliage: upper side—Elm Green, Plate 17; under side—Light Elm Green, Plate 17.
*Shape.*—Oval pointed.
*Texture.*—Upper side—leathery; glossy. Underside—smooth.
*Ribs and veins.*—Ordinary.
*Edge.*—Serrated (saw-toothed).
*Serration.*—Both double and single; small.
*Leaf stem.*—Color—Light Cress Green, Plate 31. Under side—prickly.
*Stipules.*—Medium length; smooth.
Wood:
*New Wood.*—Color—Light Cress Green, Plate 31. Bark—smooth.
*Old wood.*—Color—Jade Green, Plate 31. Bark—smooth.

Thorns:
*Thorns.*—Quantity: on main stalks from base—many; on laterals from stalk—many. Form—flat base; medium length; straight. Color (when young)—Acajou Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by its excellent plant form, its leathery and glossy foliage, its very large and well-formed buds and flowers, its two-toned bud color of Pale Orange Yellow, with the upper half of the petals lightly overcast with Thulite Pink, the distinctive Deep Rose Pink, lightly overcast with Spinel Pink color of the inside of the flower petals, the distinctive Cream color, with the outer edge of the petals lightly overcast with Cameo Pink on the reverse of the flower petals, and the distinctive Thulite Pink general color tonality of the flowers at the end of the third day.

No references cited.